US012633420B2

(12) United States Patent
Hirasawa et al.

(10) Patent No.: US 12,633,420 B2
(45) Date of Patent: May 19, 2026

(54) MANAGEMENT DEVICE, THERAPEUTIC INHALER, AND NON-TRANSITORY STORAGE MEDIUM STORING MANAGEMENT PROGRAM

(71) Applicant: OMRON HEALTHCARE Co., Ltd., Kyoto (JP)

(72) Inventors: Asa Hirasawa, Kyoto (JP); Kengo Nishiyama, Kyoto (JP); Yuka Tanabe, Kyoto (JP); Masao Maeda, Kyoto (JP); Miyuki Adachi, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 79 days.

(21) Appl. No.: 18/336,611

(22) Filed: Jun. 16, 2023

(65) Prior Publication Data

US 2023/0335295 A1       Oct. 19, 2023

Related U.S. Application Data

(63) Continuation of application No. PCT/JP2021/044540, filed on Dec. 3, 2021.

(30) Foreign Application Priority Data

Dec. 23, 2020    (JP) ................................. 2020-213867

(51) Int. Cl.
  *G16H 50/70*       (2018.01)
  *A61M 11/00*       (2006.01)
(52) U.S. Cl.
  CPC ............. *G16H 50/70* (2018.01); *A61M 11/00* (2013.01)
(58) Field of Classification Search
  CPC ............................... G16H 50/70; A61M 11/00
  See application file for complete search history.

(56) References Cited

U.S. PATENT DOCUMENTS 8,371,299 B2 *   2/2013   Denyer ................ A61M 11/005
                                              128/200.14
11,497,867 B2 *   11/2022   Costella ............ A61M 15/0021
                         (Continued)

FOREIGN PATENT DOCUMENTS

CN          102473207 A       5/2012
CN          104853690 A       8/2015
                    (Continued)

OTHER PUBLICATIONS

Chetan et al., "New Approaches to Nebulizer Drug Delivery," May 2011, The 7th International Symposium on Advanced Topics In Electrical Engineering, pp. 1-4. (Year: 2011).*
                    (Continued)

*Primary Examiner* — Kenneth Bartley
(74) *Attorney, Agent, or Firm* — Birch, Stewart, Kolasch & Birch, LLP

(57)       ABSTRACT

Provided are a management device, a therapeutic inhaler, and a non-transitory storage medium storing a management program that can appropriately manage a history of treatment using the therapeutic inhaler. A server control unit of a management server acquires operation history information of a nebulization unit of a nebulizer including first operation history information and second operation history information acquired subsequently to the first operation history information, and determines whether the first operation history information and the second operation history information are information corresponding to a case where the nebulization unit has operated for an identical treatment based on a time difference T between an ending time point of a first operation period of the nebulization unit according to the first operation history information and a starting time point of a second operation period of the nebulization unit according to the second operation history information.

12 Claims, 6 Drawing Sheets

(56) References Cited

U.S. PATENT DOCUMENTS

| 2009/0025718 | A1  | 1/2009  | Denyer et al. |
|---|---|---|---|
| 2012/0304987 | A1  | 12/2012 | Denyer et al. |
| 2013/0019860 | A1* | 1/2013  | Depla ...................... A61P 31/14 |
|  |  |  | 128/200.14 |
| 2015/0164611 | A1  | 6/2015  | Nemoto et al. |
| 2015/0283341 | A1  | 10/2015 | Adams et al. |
| 2016/0346489 | A1* | 12/2016 | Finke ...................... G08C 17/02 |
| 2018/0161531 | A1* | 6/2018  | Costella ............. G01N 15/0227 |
| 2019/0060590 | A1* | 2/2019  | Starr .................... A61B 5/0022 |

FOREIGN PATENT DOCUMENTS

| JP | 2011092418 | A | * | 5/2011 |
|---|---|---|---|---|
| JP | 2017527868 | A | * | 9/2017 |
| JP | 2018000322 | A | * | 1/2018 |
| JP | 2019504696 | A | * | 2/2019 |
| JP | 2020500639 | A | * | 1/2020 |
| WO | WO-2022138084 | A1 | * | 6/2022 |

OTHER PUBLICATIONS

International Search Report for International Application No. PCT/JP2021/044540, Dated Jan. 25, 2022.

International Preliminary Report (IPRP) Issued for International Application No. PCT/JP2021/044540, Dated Aug. 24, 2022.

Chinese Office Action and Search Report for Chinese Application No. 202180082767.1, dated Jan. 26, 2026, with English translation.

* cited by examiner

[FIG. 1]
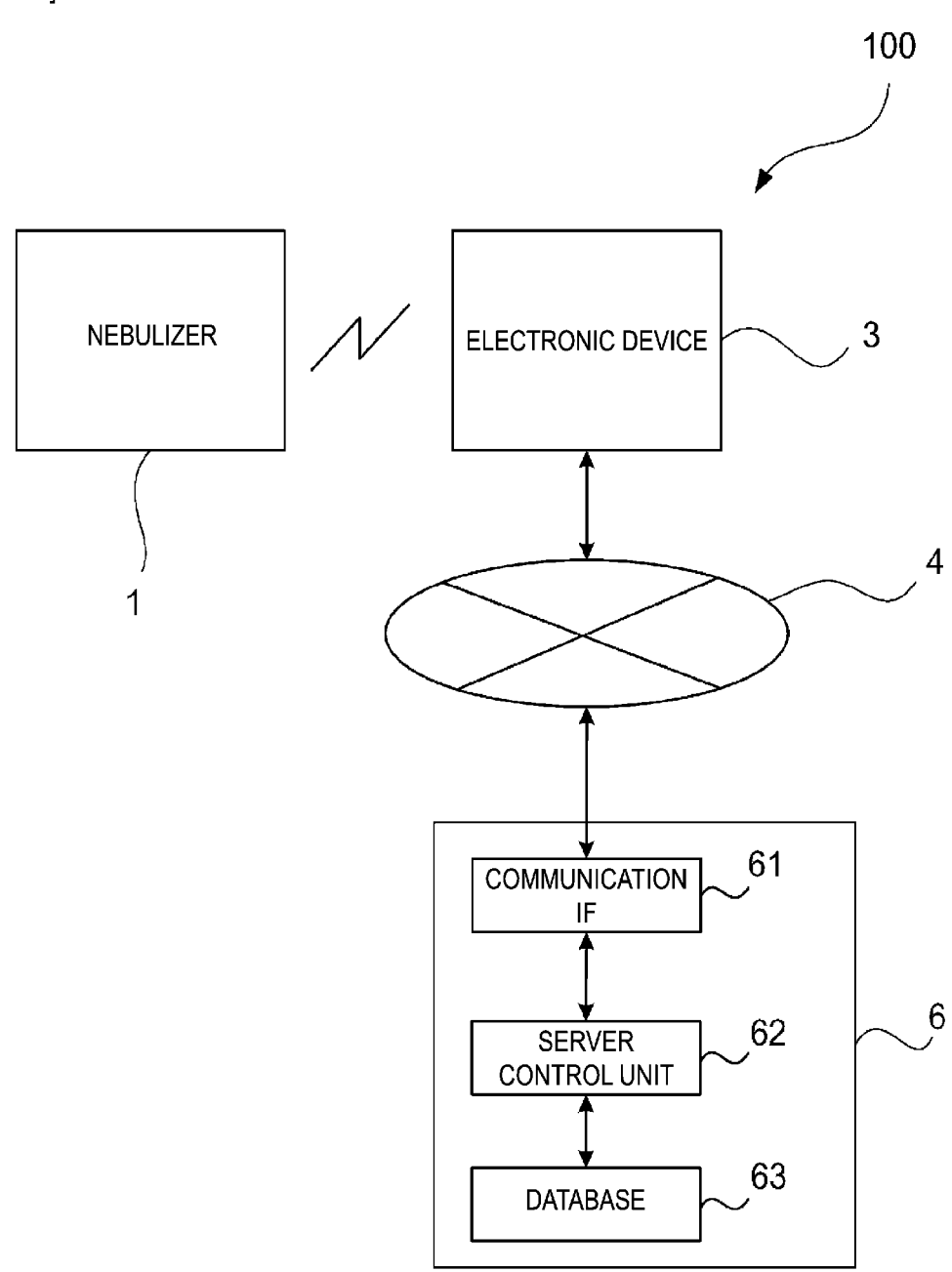

[FIG. 2]
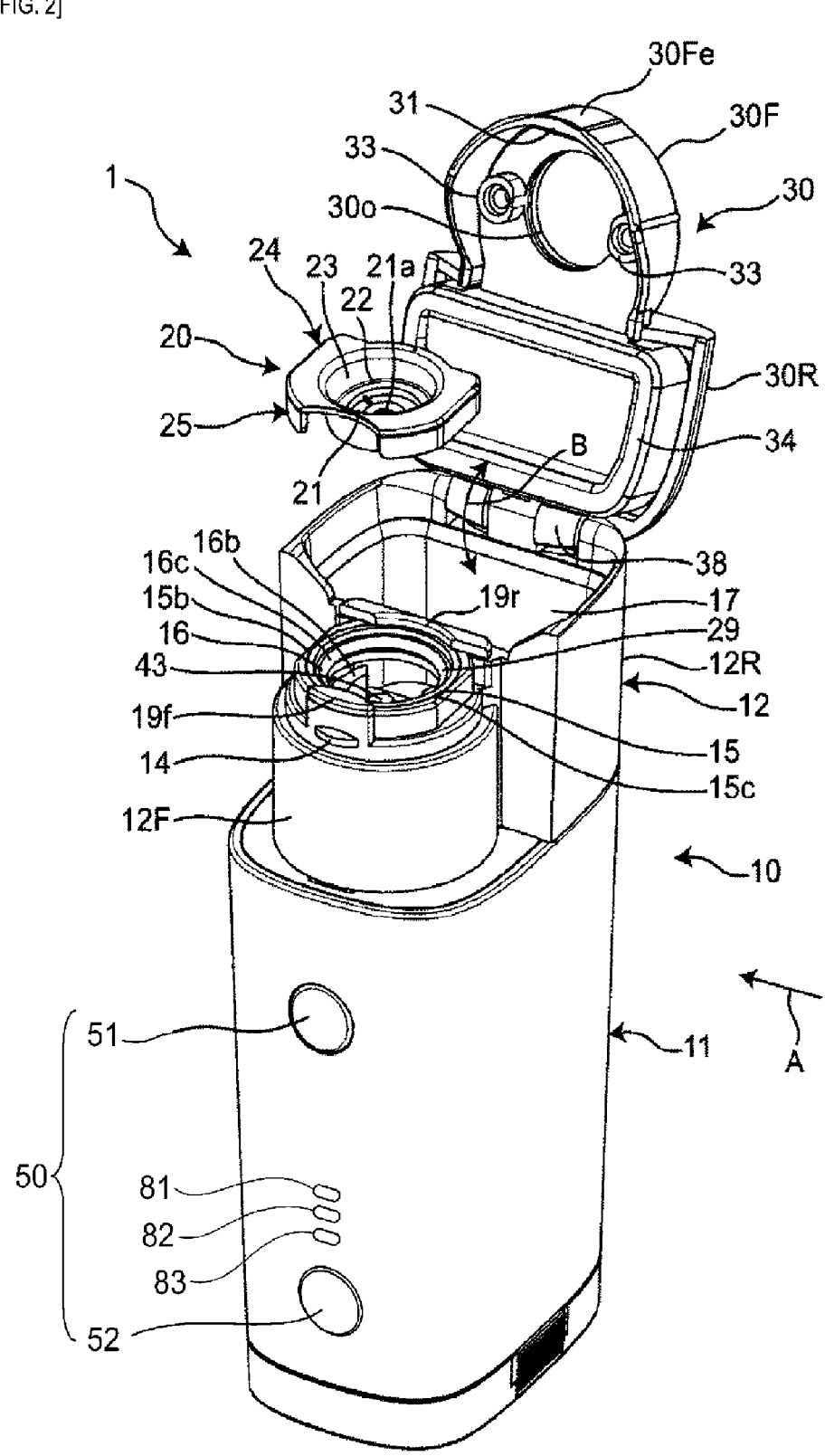

[FIG. 3]
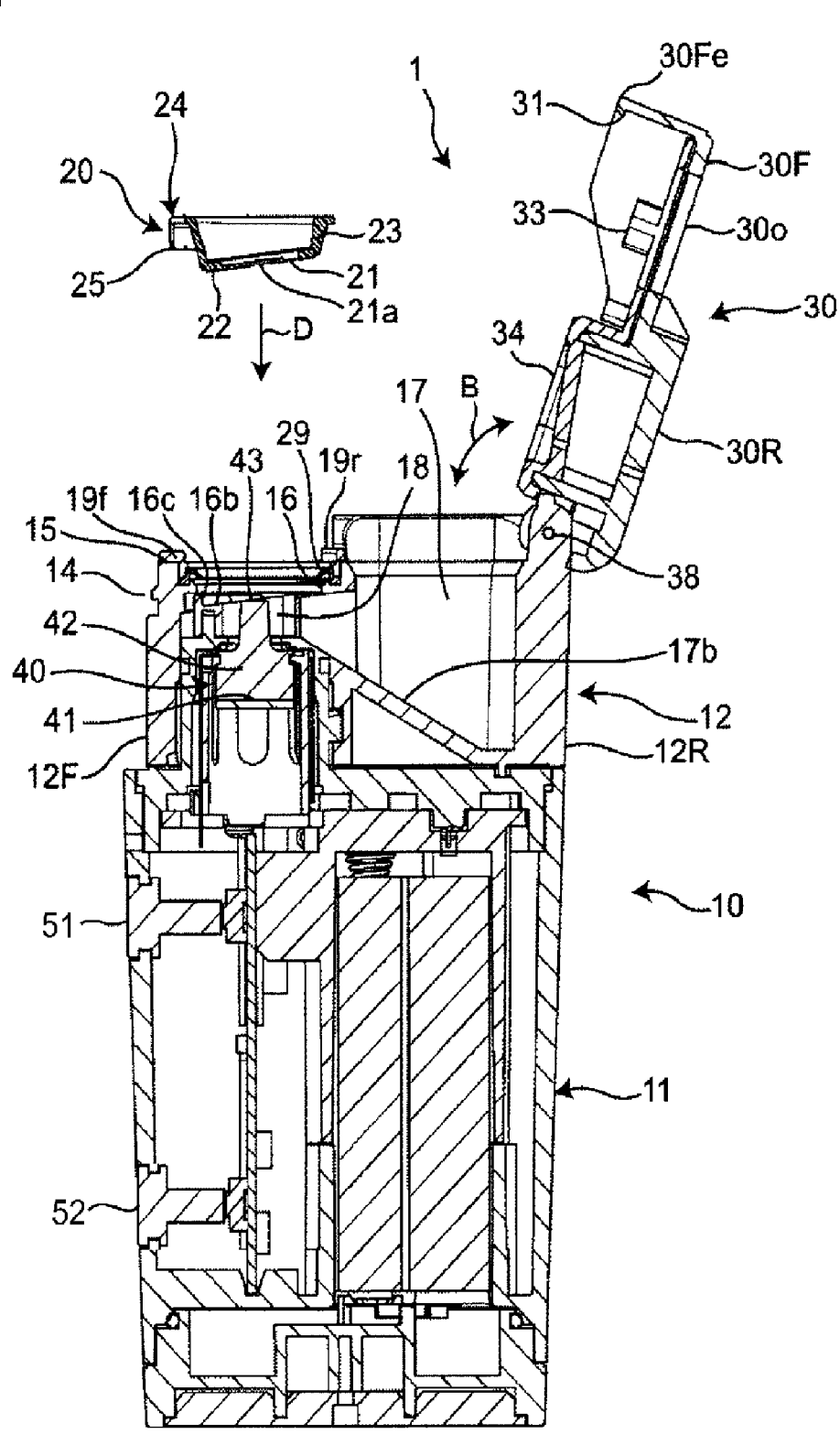

[FIG. 4]

[FIG. 5]
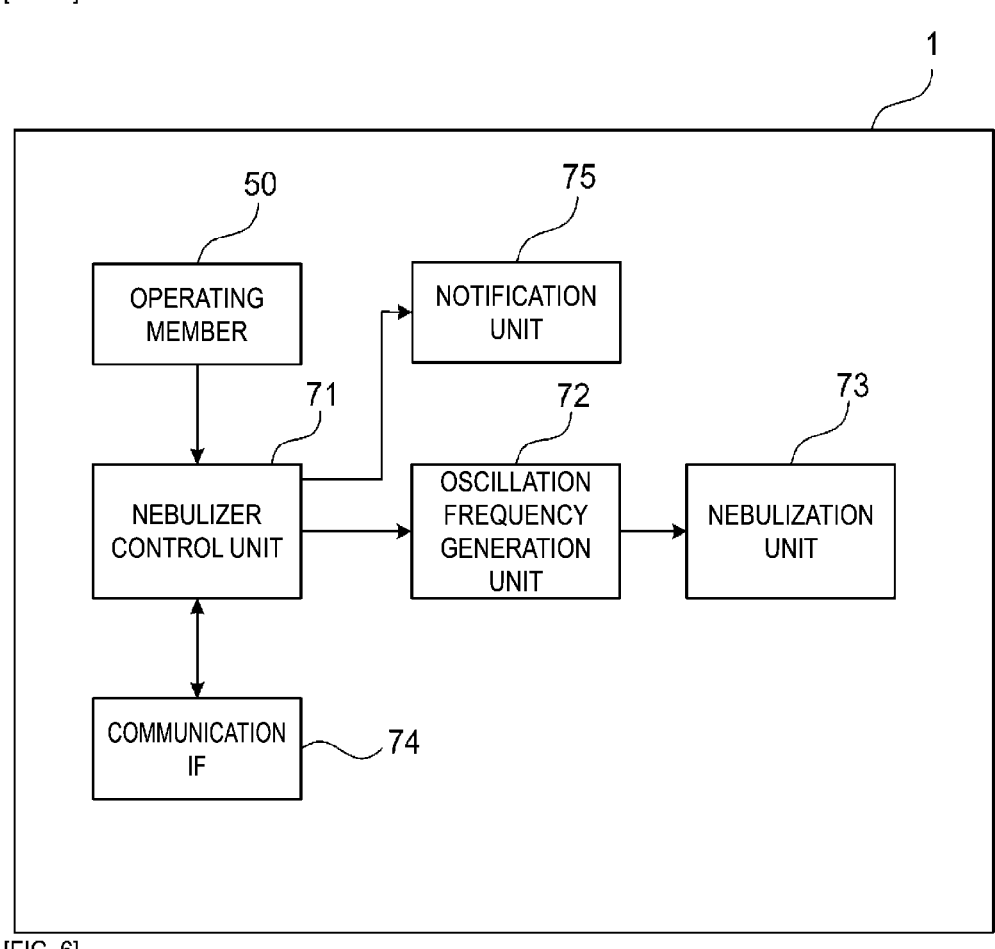
[FIG. 6]
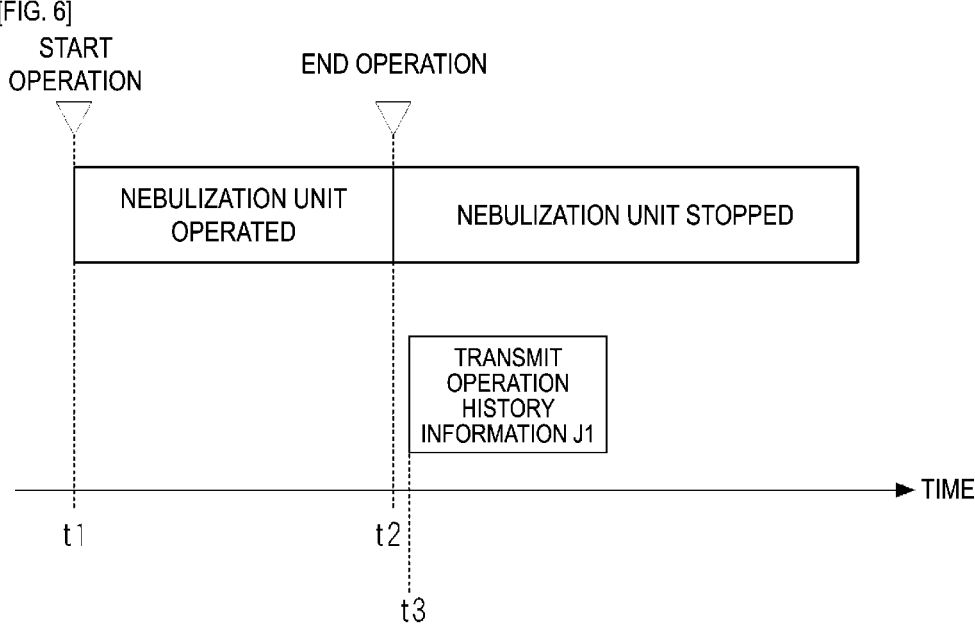

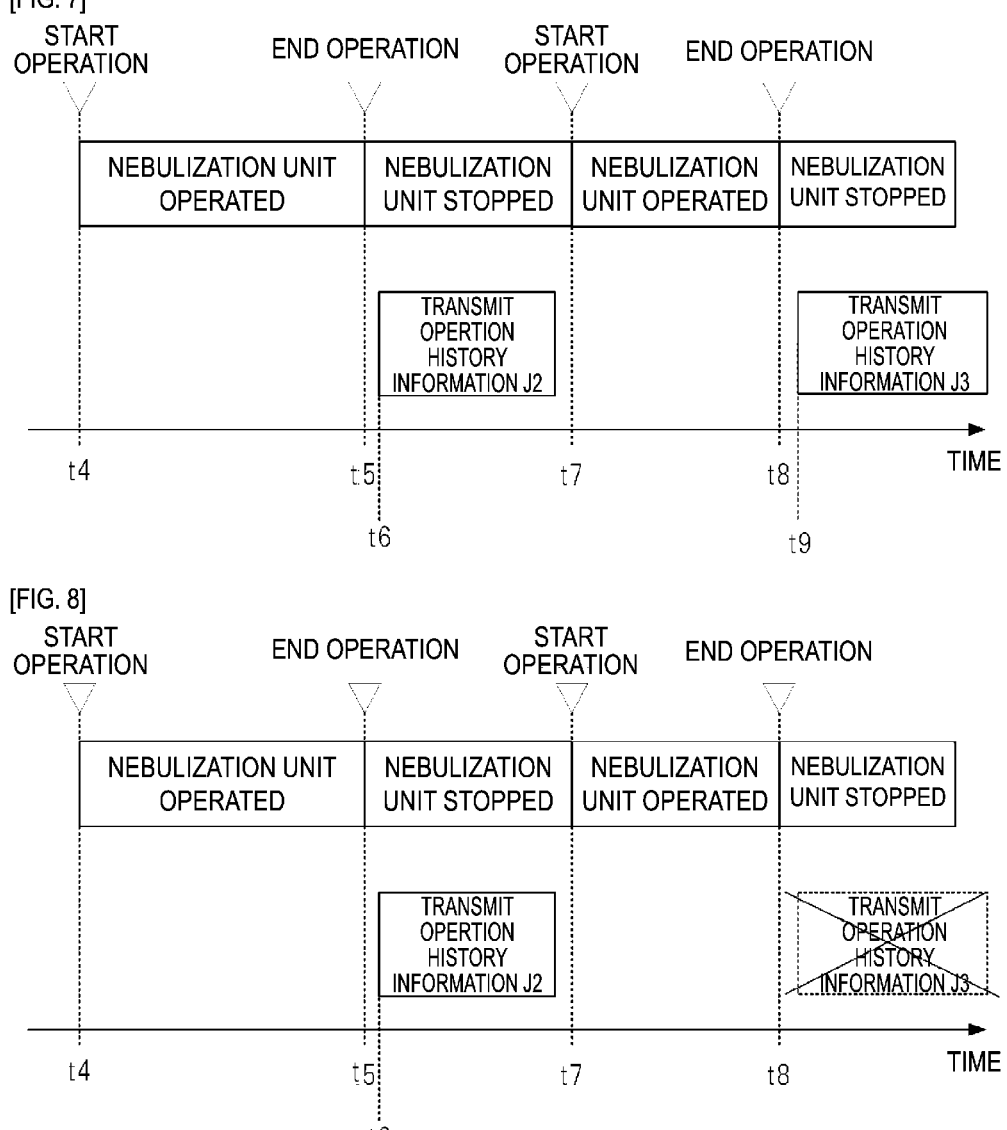
[FIG. 7]

MANAGEMENT DEVICE, THERAPEUTIC INHALER, AND NON-TRANSITORY STORAGE MEDIUM STORING MANAGEMENT PROGRAM

CROSS-REFERENCE TO RELATED APPLICATIONS

This application is the U.S. national stage application filed pursuant to 35 U.S.C. 365(c) and 120 as a continuation of International Patent Application No. PCT/JP2021/044540, filed Dec. 3, 2021, which application claims priority to Japanese Patent Application No. 2020-213867, filed Dec. 23, 2020, which applications are incorporated herein by reference in their entireties.

TECHNICAL FIELD

The present invention relates to a management device, a therapeutic inhaler, and a non-transitory storage medium storing a management program.

BACKGROUND ART

Patent Document 1 describes a system including a nebulizer and a computer. In the nebulizer, when a start key is pressed, administration of a medical agent is started by a nebulizer part and a start notice is transmitted to the computer, and when a stop key is pressed, a stop notice is transmitted to the computer.

Patent Document 2 describes an asthma treatment support system appropriate for transmitting, managing, and displaying the usage status of a portable inhaler of an aerosol type (pressurized metered dose type). In this system, when a transmission device attached to the inhaler detects an operation of a can containing a medical agent by a user's finger, the transmission device calculates usage count information of the inhaler based on the detection result and transmits the usage count information to a management server.

CITATION LIST

Patent Literature

Patent Document 1: JP 2018-000322 A
Patent Document 2: JP 2011-092418 A

SUMMARY OF INVENTION

Technical Problem

A treatment using a therapeutic inhaler such as a nebulizer configured to enable the inhalation of a nebulized medicinal solution is required to be performed at a frequency designated by a physician. Here, one treatment using the therapeutic inhaler means that an action of inhaling the same kind of medical agent is performed for a predetermined period of time (for example, for five minutes or the like). For example, if the operation history of the therapeutic inhaler can be confirmed later by the physician, the physician can determine whether the treatment was performed at an appropriate frequency, which is helpful for determining a treatment strategy.

Such a therapeutic inhaler is often used for children including infants and toddlers. However, it is difficult for children to remain stationary for a long period of time. Therefore, even in a case where one treatment is performed, a usage state is assumed in which nebulization and inhalation of a medicinal solution are started and subsequently the inhalation and the nebulization are interrupted, and after a while, the nebulization and the inhalation are resumed. In order to determine whether the treatment was performed at an appropriate frequency, it is preferable to separately manage the temporary stop of the nebulization due to the above-described interruption and the stop of the nebulization upon completion of the treatment.

An object of the present invention is to provide a management device, a therapeutic inhaler, and a non-transitory storage medium storing a management program that can appropriately manage a history of a treatment using the therapeutic inhaler.

Solution to Problem (1)

A management device including a processor, the processor being configured to acquire operation history information of a nebulization unit in a therapeutic inhaler enabling inhalation of a medicinal solution nebulized by the nebulization unit, the operation history information including first operation history information and second operation history information acquired subsequently to the first operation history information, and determine whether the first operation history information and the second operation history information are information corresponding to a case where the nebulization unit has operated for an identical treatment based on a time difference between an ending time point of a first operation period of the nebulization unit according to the first operation history information and a starting time point of a second operation period of the nebulization unit according to the second operation history information.

According to (1), for example, when the time difference between the ending time point of the first operation period and the starting time point of the second operation period is long, it can be determined that the nebulization unit has operated for different treatments during the first operation period and the second operation period. On the other hand, when the time difference is short, it can be determined that the nebulization unit has operated for an identical treatment during the first operation period and the second operation period, but the operation of the nebulization unit has been temporarily interrupted. In this way, it can be determined whether a treatment has been interrupted based on an interval between respective operation periods of the nebulization unit which have successively operated. By using this determination result, the frequency of the treatment using the therapeutic inhaler can be accurately grasped, which is helpful for determining a treatment strategy.

(2)

The management device according to (1), wherein the processor determines that the first operation history information and the second operation history information are information corresponding to a case where the nebulization unit has operated for different treatments when the time difference is equal to or longer than a threshold value, or determines that the first operation history information and the second operation history information are information corresponding to a case where the nebulization unit has operated for an identical treatment when the time difference is shorter than the threshold value.

According to (2), the frequency of the treatment using the therapeutic inhaler can be accurately grasped, which is helpful for determining a treatment strategy.

(3)

The management device according to (1), wherein the operation history information includes medicinal solution type information indicating a type of medicinal solution nebulized by the nebulization unit during an operation period of the nebulization unit, and the processor determines whether the first operation history information and the second operation history information are information corresponding to a case where the nebulization unit has operated for an identical treatment based on the time difference, the medicinal solution type information included in the first operation history information, and the medicinal solution type information included in the second operation history information.

For example, even when the time difference between the ending time point of the first operation period and the starting time point of the second operation period is short, if the types of medicinal solutions nebulized during these two operation periods are different from each other, it can be determined that the nebulization unit has operated for different treatments during the first operation period and the second operation period. As described in (3), whether the treatment has been interrupted can be determined with higher accuracy by considering not only the interval between the operation periods of the nebulization unit which has successively operated, but also the type of medicinal solution nebulized during each of the operation periods.

(4)

The management device according to (3), wherein the processor determines that the first operation history information and the second operation history information are information corresponding to a case where the nebulization unit has operated for different treatments when the time difference is shorter than a threshold value and the medicinal solution type information included in the first operation history information differs from the medicinal solution type information included in the second operation hi story information.

According to (4), the frequency of the treatment using the therapeutic inhaler can be more accurately grasped, which is helpful for determining a treatment strategy.

(5)

The management device according to any one of (1) to (4), wherein upon determining that a plurality of pieces of the operation history information are information corresponding to a case where the nebulization unit has operated for an identical treatment, the processor deletes the plurality of pieces of the operation history information except for one of the plurality of pieces of the operation history information or combines the plurality of pieces of the operation history information.

According to (5), it is possible to delete or combine the operation history information which has generated due to the interruption of the treatment and is not required to be managed. Accordingly, the amount of data to be retained can be reduced.

(6)

The management device according to any one of (1) to (4), wherein upon determining that the first operation history information and the second operation history information are information corresponding to a case where the nebulization unit has operated for an identical treatment, the processor records the first operation history information and the second operation history information in association with common identification information.

According to (6), by referring to the identification information associated with the operation history information, the number of times of the treatment performed can be accurately grasped. In this way, the frequency of the treatment using the therapeutic inhaler can be accurately grasped, which is helpful for determining a treatment strategy.

(7)

The management device according to (6), further including a communication unit configured to communicate with the therapeutic inhaler, wherein the processor acquires the operation history information from the therapeutic inhaler via the communication unit, makes a request to a user terminal to confirm whether correction of a plurality of pieces of the operation history information associated with the common identification information is necessary, and, upon determining that the correction is necessary based on a response to the request, corrects the plurality of pieces of the operation history information.

According to (7), a user of the user terminal confirms whether the correction is necessary, and when the user determines that the correction is necessary, the plurality of pieces of the operation history information are corrected. Accordingly, it is possible to prevent, with high accuracy, the plurality of pieces of the operation history information from being corrected despite the absence of the interruption of the treatment. As a result, the frequency at which the treatment has been performed can be more accurately provided to a physician.

(8)

The management device according to (7), wherein the processor performs the correction by deleting the plurality of pieces of the operation history information except for one of the plurality of pieces of the operation history information, or performs the correction by combining the plurality of pieces of the operation history information.

According to (8), it is possible to delete or combine the operation history information which has been generated due to the interruption of the treatment and is not required to be managed while reflecting the intention of the user of the user terminal. Accordingly, the frequency at which the treatment has been performed can be more accurately provided to a physician.

(9)

The management device according to any one of (1) to (6), further including a communication unit configured to communicate with the therapeutic inhaler, wherein the processor acquires the operation history information from the therapeutic inhaler via the communication unit.

According to (9), the therapeutic inhaler only needs to have a function of transmitting the operation history information. Accordingly, the manufacturing cost of the therapeutic inhaler can be reduced.

(10)

A therapeutic inhaler including:

the management device according to any one of (1) to (4); and the nebulization unit, the processor being configured to control transmission of the operation history information to an external device, and, upon determining that the first operation history information and the second operation history information are information corresponding to a case where the nebulization unit has operated for an identical treatment at a time point before the transmission of the second operation history information to the external device, omit the transmission of the second operation history information to the external device.

According to (10), data based on the operation history information for each treatment can be presented to a physician or the like by the external device. In this case, the external device only needs to have a function of outputting the data based on the operation history information received from the therapeutic inhaler. Accordingly, the construction cost of a system including the therapeutic inhaler and the external device can be reduced.

(11)

A therapeutic inhaler configured to enable inhalation of medicinal solution nebulized by a nebulization unit, the therapeutic inhaler including:

a communication unit configured to be communicable with the management device according to any one of (1) to (9);

an operating member configured to enable a start operation for instructing a start of nebulization by the nebulization unit and an end operation for instructing an end of the nebulization by the nebulization unit; and an inhaler processor configured to transmit operation history information of the nebulization unit to the management device, the inhaler processor transmitting at least part of the operation history information to the management device at a time point after the nebulization unit is stopped in response to the end operation.

According to (11), at least part of the operation history information is transmitted to the management device in a state where the nebulization unit is stopped. Accordingly, the information can be stably transmitted, and necessary information can be transmitted to the management device.

(12)

The therapeutic inhaler according to (11), wherein the inhaler processor transmits all of the operation history information to the management device at the time point.

According to (12), the operation history information available for the management of the treatment using the therapeutic inhaler can be transmitted to the management device without omission.

(13)

The therapeutic inhaler according to (12), wherein when a time point of performing the start operation is defined as a starting time point, a time point of performing the end operation is defined as an ending time point, and a time difference from the starting time point to the ending time point is defined as an operation time period, then the operation history information includes the starting time point and the operation time period, or the ending time point and the operation time period, or the starting time point and the ending time point.

According to (13), at least the time point at which the treatment using the therapeutic inhaler has been performed and the time period during which the treatment has been performed can be managed by the management device. Accordingly, it is possible to determine whether the treatment has been performed at an appropriate frequency and with an appropriate amount of medicinal solution.

(14)

The therapeutic inhaler according to (13), wherein the operation history information includes information about a type of medicinal solution nebulized by the nebulization unit.

According to (14), in a case where a patient who receives a treatment using a plurality of medicinal solutions uses the therapeutic inhaler, it is possible to determine whether the patient appropriately inhaled the medicinal solutions.

(15)

A non-transitory storage medium storing a management program for managing a treatment using a therapeutic inhaler configured to enable inhalation of a medicinal solution nebulized by a nebulization unit, the management program causing a computer to execute processing, the processing including:

acquiring operation history information of the nebulization unit, the operation history information including first operation history information and second operation history information acquired subsequently to the first operation history information; and determining whether the first operation history information and the second operation history information are information corresponding to a case where the nebulization unit has operated for an identical treatment based on a time difference between an ending point of a first operation period of the nebulization unit according to the first operation history information and a starting time point of a second operation period of the nebulization unit according to the second operation history information.

According to (15), effects similar to those in (1) can be achieved.

Advantageous Effects of Invention

According to the present invention, the history of a treatment using a therapeutic inhaler can be appropriately managed.

BRIEF DESCRIPTION OF DRAWINGS

FIG. 1 is a schematic diagram illustrating an outline configuration of a treatment management system.

FIG. 2 is an exploded perspective view of a nebulizer illustrated in FIG. 1.

FIG. 3 is a vertical cross-sectional view of the nebulizer illustrated in FIG. 2 as viewed from the right side (the direction indicated by an arrow A in FIG. 2).

FIG. 4 is a schematic diagram illustrating a usage state of the nebulizer illustrated in FIG. 1.

FIG. 5 is a diagram illustrating a block configuration of the nebulizer illustrated in FIG. 1.

FIG. 6 is a timing chart for explaining the operation of a nebulizer control unit when a treatment is completed by a single operation of a nebulization unit.

FIG. 7 is a timing chart for explaining the operation of the nebulizer control unit when a treatment is completed by two operations of the nebulization unit (when the treatment is interrupted once).

FIG. 8 is a timing chart for explaining a modification of the operation of the nebulizer control unit when a treatment is completed by two operations of the nebulization unit.

DESCRIPTION OF EMBODIMENTS

Overview

The overview of a treatment management system including a server which is an embodiment of a management device of the present invention and a nebulizer which is an embodiment of a therapeutic inhaler of the present invention will be described. The nebulizer transmits, to the server, operation history information of a nebulization unit relating to the operation of the nebulization unit. The server acquires the operation history information of the nebulization unit of the nebulizer including first operation history information and second operation history information acquired subsequently to the first operation history information, and based on a time difference between an ending time point of a first operation period of the nebulization unit according to the first operation history information and a starting time point of a second operation period of the nebulization unit according to the second operation history information, determines whether the first operation period and the second operation period are periods during which the nebulization unit has operated for an identical treatment. For example, when the time difference is equal to or shorter than a threshold value, the server determines that two operations of the nebulization unit has been performed for an identical treatment. Upon determining that the first operation period and the second operation period are periods during which the nebulization unit has operated for an identical treatment, the server combines the operation history information corresponding to the first operation period and the operation history information corresponding to the second operation period, or deletes the operation history information corresponding to the second operation period, for example. Accordingly, it is possible to prevent a single treatment performed by operating the nebulization unit a plurality of times from being recognized as a plurality of treatments, and accurately grasp the frequency of the treatment using the nebulizer. An embodiment of a treatment management system including a nebulizer will be described in detail below.

EMBODIMENT

Configuration of Treatment Management System

FIG. 1 is a schematic diagram illustrating an outline configuration of a treatment management system 100. The treatment management system 100 includes a nebulizer 1 as a therapeutic inhaler for treating a respiratory disease by inhaling a nebulized medicinal solution, an electronic device 3 held by a user of the nebulizer 1 or a person related to the user (for example, a parent of the user), and a management server 6 as a management device.

The electronic device 3 is an electronic device having a communication function, such as a personal computer, a smartphone, or a tablet terminal. The electronic device 3 is configured to be communicable with the management server 6 via a network 4 such as the Internet. The electronic device 3 is configured to be communicable with the nebulizer 1 based on a short-range communication standard such as Bluetooth (trade name) or Wi-Fi.

A treatment management application provided by an operator of the treatment management system 100 is installed in the electronic device 3. The function of the treatment management application enables transmission and reception of information between the nebulizer 1 and the electronic device 3, transmission of information from the electronic device 3 to the management server 6, viewing of display data generated by the management server 6 via the electronic device 3, and the like.

Block Configuration of Management Server

As illustrated in FIG. 1, the management server 6 includes a communication interface (IF) 61 (communication unit) for performing communication with a device connected to the network 4, a server control unit 62, and a database 63. The database 63 may be a storage externally attached to the management server 6 or a network storage connected to the network 4.

The server control unit 62 comprehensively controls the entire management server 6, and includes a processor such as a central processing unit (CPU) that implements a program to perform processing, a read only memory (ROM) that stores the program or the like implemented by the processor, and a random access memory (RAM) as a working memory. Specifically, the structure of the processor described in the present specification is an electric circuit in which circuit elements such as semiconductor elements are combined.

The server control unit 62 acquires information transmitted from the nebulizer 1 to the electronic device 3 and transferred from the electronic device 3 via the communication interface 61, and records the acquired information in the database 63. The server control unit 62 processes the information recorded in the database 63 to generate display data for displaying treatment results such as a time point of a treatment performed using the nebulizer 1 (treatment time point) and a time duration during which the treatment has been performed (treatment time). Upon receipt of a request for viewing the display data from the electronic device 3 or another electronic device connected to the network 4 (for example, a device operated by a physician who examines the user of the nebulizer 1), the server control unit 62 performs control to cause the requesting electronic device to display an image based on the display data.

Structure of Nebulizer

FIG. 2 is an exploded perspective view of the nebulizer 1 illustrated in FIG. 1. FIG. 3 is a vertical cross-sectional view of the nebulizer 1 illustrated in FIG. 2 as viewed from the right side (the direction indicated by an arrow A in FIG. 2).

As illustrated in FIGS. 2 and 3, the nebulizer 1 includes a main body 10 including a lower body portion 11 having a substantially elliptic columnar outer shape and an upper body portion 12 removably fitted and attached to the lower body portion 11 from above, an attachment member 20 attached to the upper body portion 12, and a cap member 30 configured to be openable and closable with respect to the upper body portion 12. A front half portion 12F of the upper body portion 12 has a substantially columnar outer shape, and a rear half portion 12R of the upper body portion 12 has a substantially trapezoidal columnar outer shape.

As illustrated in FIG. 2, an operating member 50 including a start/end button 51 and a medicinal solution selection button 52, and light emitting portions 81, 82, and 83 for making a notification of a type of a medicinal solution being selected by the medicinal solution selection button 52 are provided on a front surface of the lower body portion 11.

As illustrated in FIG. 3, an upper surface of the front half portion 12F of the upper body portion 12 is provided with a recessed portion 16 having a substantially circular planar shape which opens upward so as to receive the attachment member 20. The recessed portion 16 includes a bottom surface 16b inclined with respect to a vertical axis direction (vertical direction) of the main body 10, and a side surface 16c which is continuous with the bottom surface 16b and gradually opened upward. Raised portions 19f and 19r are provided at specific orientations (in this example, on the front side and the rear side) of an edge 15 surrounding the recessed portion 16. The raised portion 19f on the front side has a planar shape protruding in an arc shape toward the center of the recessed portion 16. The raised portion 19r on the rear side has a planar shape recessed in an arc shape as viewed from the center of the recessed portion 16. The raised portions 19*f* and 19*r* are intended to be fitted with a flange 24 of the attachment member 20. Further, a packing 29 made of an annular elastic body is provided on the side surface 16*c* of the recessed portion 16 so as to surround and contact a sidewall 23 of the attachment member 20 in a circumferential direction.

As illustrated in FIG. 3, a vibrating portion 40 is provided inside the front half portion 12F of the upper body portion 12 at a position corresponding to the recessed portion 16. The vibrating portion 40 includes an ultrasonic vibrator 41 disposed at a position separated downward from the recessed portion 16, a vibrating surface 43 disposed horizontally at a position corresponding to the bottom surface 16*b* of the recessed portion 16, and a horn 42 disposed between the ultrasonic vibrator 41 and the vibrating surface 43 to amplify the vibration of the ultrasonic vibrator 41 and transmit the vibration to the vibrating surface 43. A drive voltage for the ultrasonic vibrator 41 is supplied from the lower body portion 11 via a contact electrode provided between the upper body portion 12 and the lower body portion 11.

As illustrated in FIG. 2, a liquid storage 17 having a substantially semicircular planar shape is provided at the rear half portion 12R of the upper body portion 12. As illustrated in FIG. 3, the liquid storage 17 includes a bottom surface 17*b* which becomes gradually shallower toward the front side. A liquid supply path 18 for supplying a liquid (medicinal solution) from the liquid storage 17 onto the vibrating surface 43 of the vibrating portion 40 is provided so as to be continuous with a front surface side portion of the liquid storage 17. In a disassembled state in FIGS. 2 and 3, the liquid storage 17 opens upward. Thus, the user can put a liquid such as a medicinal solution into the liquid storage 17 from above.

The cap member 30 serving as a cover is connected to an upper edge on a rear end side of the rear half portion 12R of the upper body portion 12 so as to be rotatable with respect to the upper body portion 12 via a hinge 38. The cap member 30 includes a rear half portion 30R which is disposed on a side close to the hinge 38 and has a substantially trapezoidal planar shape, and a front half portion 30F which is continuous with the rear half portion 30R and has substantially circular planar shape. Two protrusions 33 having a cylindrical shape are protrudingly provided at the front half portion 30F of the cap member 30 on a side facing the upper surface of the upper body portion 12 at positions corresponding to a left-side portion 15*b* and a right-side portion 15*c* of the edge 15 surrounding the recessed portion 16. A mesa portion 34 having a substantially trapezoidal planar shape corresponding to the planar shape of the liquid storage 17 is provided at the rear half portion 30R of the cap member 30 on a side facing the upper surface of the upper body portion 12. In a state where the cap member is closed with respect to the upper body portion 12 and the nebulizer 1 is assembled, the protrusions 33 function to position the attachment member 20. Further, the mesa portion 34 closes the upper portion of the liquid storage 17 to prevent a medicinal solution from overflowing from the liquid storage 17. The center of the front half portion 30F of the cap member 30 is an opening 30*o* to which a mouthpiece or the like is to be attached.

An engagement projection 31 projecting inward is provided at a front edge 30Fe (on a side opposite to the hinge 38) of the front half portion 30F of the cap member 30. On the other hand, an engagement projection 14 is provided at the front half portion 12F of the upper body portion 12 so as to project outward (forward) from the front end of the front half portion 12F. When the cap member 30 is closed with respect to the upper body portion 12, the engagement projection 31 of the cap member 30 engages with the engagement projection 14 of the upper body portion 12 in the vertical direction.

The attachment member 20 is attached to the recessed portion 16 of the upper body portion 12 when the nebulizer 1 is used. The attachment member 20 includes a sheet 21 having a flat film-like shape to face the vibrating surface 43, a bottom plate 22 supporting the sheet 21, the sidewall 23 having an annular shape which is continuous with an outer edge of the bottom plate 22 to face the side surface 16*c* of the recessed portion 16, the flange 24 which is continuous with an upper edge of the sidewall 23 and extends radially outward around the upper edge, and a tab 25 which is continuous with a part of an outer edge of the flange 24 and extends downward. The sheet 21 is attached to the lower surface of the bottom plate 22 by adhesion or welding. A substantially central region of the sheet 21 constitutes a mesh portion 21*a*.

Assembly of Nebulizer

In a state where the cap member 30 is opened with respect to the main body 10, a user who intends to use the nebulizer 1 attaches the attachment member 20 including the mesh portion 21*a* to the recessed portion 16 having a shape opening upward in the main body 10 as indicated by an arrow D in FIG. 3. In a state where the attachment member 20 is attached, the user turns and closes the cap member 30 via the hinge 38 with respect to the main body 10 (the upper body portion 12). Then, the engagement projection 31 of the cap member 30 is engaged with the engagement projection 14 of the upper body portion 12 in the vertical direction. Accordingly, the cap member 30 is fixed to the upper body portion 12 in a closed state. In this way, the nebulizer 1 is easily assembled. This state is referred to as an assembled state.

Use of Nebulizer

Figure 4:
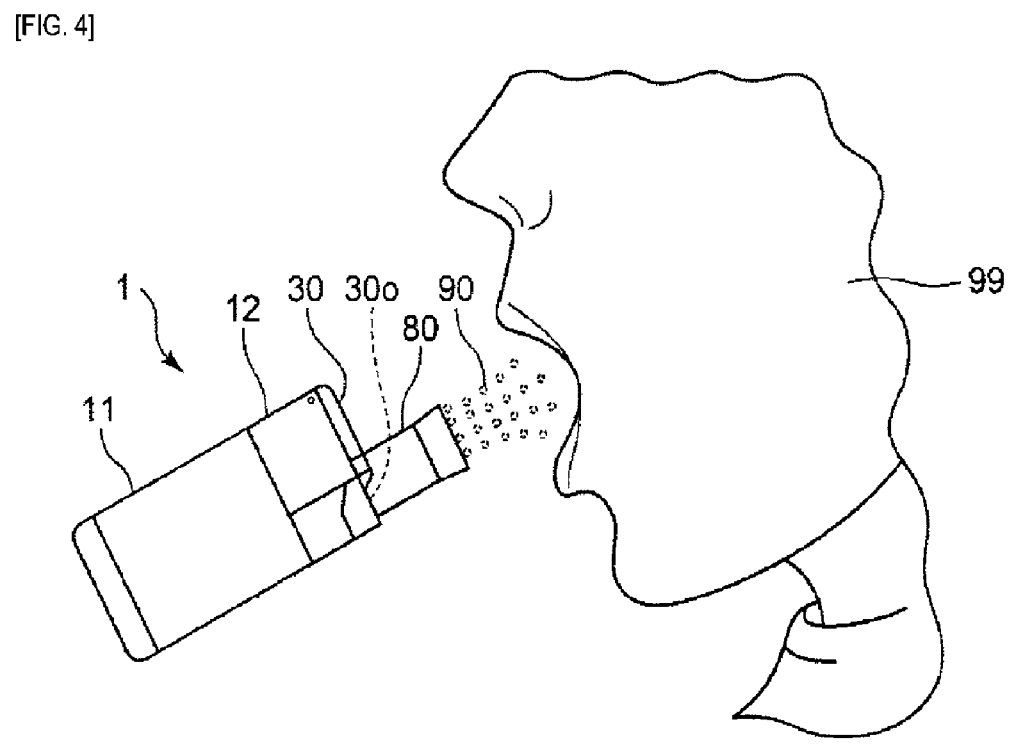

Before using the nebulizer 1, the user puts a medicinal solution in the liquid storage 17 of the upper body portion 12. Then, as illustrated in FIG. 4, the user attaches, for example, a mouthpiece 80 to the opening 30*o* of the cap member 30 in the assembled state. Instead of the mouthpiece 80, an inhalation mask covering the face of a user 99 may be attached.

As illustrated in FIG. 4, when the nebulizer 1 is slightly tilted to the front side, the medicinal solution is supplied from the liquid storage 17 onto the vibrating surface 43 of the vibrating portion 40 through the liquid supply path 18. That is, the medicinal solution is supplied between the vibrating surface 43 and the mesh portion 21*a*. In this state, when a drive voltage is applied to the ultrasonic vibrator 41 of the vibrating portion 40 and the vibrating surface 43 is vibrated, a medicinal solution 90 is nebulized and sprayed through the mesh portion 21*a* (more accurately, a plurality of through holes penetrating the sheet 21). In this way, the vibrating portion 40 and the mesh portion 21*a* of the attachment member 20 constitute a nebulization unit (a nebulization unit 73 to be described later) that nebulizes a liquid such as a medicinal solution stored in the liquid storage 17.

Block Configuration of Nebulizer

FIG. 5 is a diagram illustrating a block configuration of the nebulizer 1. The nebulizer 1 includes the operating member 50, a nebulizer control unit 71, an oscillation frequency generation unit 72, the nebulization unit 73, a communication interface 74 constituting the communication unit for communicating with the electronic device 3, and a notification unit 75.

The start/end button 51 included in the operating member 50 is an operating member that enables a start operation for instructing the nebulizer control unit 71 to start the operation of the nebulization unit 73 and an end operation for instructing the nebulizer control unit 71 to stop the operation of the nebulization unit 73. For example, a short-press operation of the start/end button 51 in a state where the nebulization unit 73 is not in operation is the start operation, and a short-press operation of the start/end button 51 after the start operation is the end operation. The start/end button 51 may be divided into two buttons, that is, a button for enabling the start operation and a button for enabling the end operation.

The medicinal solution selection button 52 included in the operating member 50 is an operating member for enabling the user to select a type of medicinal solution to be used for the treatment using the nebulizer 1.

The notification unit 75 includes the light emitting portions 81, 82, and 83 illustrated in FIG. 2. Each of the light emitting portions 81, 82, and 83 includes a light emitting element such as light emitting diode (LED). By the function of the treatment management application installed in the electronic device 3, information about different medicinal solution types can be registered in association with the light emitting portions 81, 82, and 83, respectively. Each time the user operates the medicinal solution selection button 52, a state in which the light emitting portion 81 is lighted, a state in which the light emitting portion 82 is lighted, and a state in which the light emitting portion 83 is lighted are sequentially switched. Then, the type of medicinal solution associated with the light emitting portion that is lighted is recognized by the nebulizer control unit 71 as the medicinal solution selected by the user.

The oscillation frequency generation unit 72 applies an AC drive voltage to the ultrasonic vibrator 41 of the vibrating portion 40 based on a control signal from the nebulizer control unit 71. In the present specification, a state where a drive voltage is applied to the ultrasonic vibrator 41 is referred to as a state where the nebulization unit 73 is in operation, and a state where no drive voltage is applied to the ultrasonic vibrator 41 is referred to as a state where the nebulization unit 73 is stopped.

The nebulizer control unit 71 includes a processor such as a CPU, a RAM serving as a working memory, and a ROM for recording various types of information, and performs various types of processing by the processor. The nebulizer control unit 71 activates the nebulization unit 73 upon detecting the start operation in a state where the nebulization unit 73 is not in operation, and stops the nebulization unit 73 upon detecting the end operation in a state where the nebulization unit 73 is in operation. When the nebulization unit 73 is activated, the nebulizer control unit 71 performs control to transmit operation history information of the nebulization unit 73 relating to the operation thereof to the management server 6 via the electronic device 3.

In the following description, the nebulizer control unit 71 considers a time point (specifically, date and time) at which the start operation is detected, as an operation starting time point of the nebulization unit 73. In addition, the nebulizer control unit 71 considers a time point (specifically, date and time) at which the end operation is detected as an operation ending time point of the nebulization unit 73. Further, the nebulizer control unit 71 considers a time difference from an operation starting time point to an immediately subsequent operation ending time point as an operation time period of the nebulization unit 73. An operation starting time point, an operation ending time point, and an operation time period constitute the operation history information of the nebulization unit 73.

FIG. 6 is a timing chart for explaining the operation of the nebulizer control unit 71 when a treatment is completed by a single operation of the nebulization unit 73.

Upon detecting the start operation at a time point t1, the nebulizer control unit 71 activates the nebulization unit 73, and upon detecting the end operation at a time point t2, the nebulizer control unit 71 stops the operation of the nebulization unit 73. In addition, upon detecting the end operation at the time point t2, the nebulizer control unit 71 generates operation history information J1 relating to the operation of the nebulization unit 73 started at the time point t1. The operation history information J1 includes three types of information, that is, the time point t1 (operation starting time point), a time difference between the time point t1 and the time point t2 (operation time period of the nebulization unit 73), and a type of medicinal solution nebulized by the nebulization unit 73. The nebulizer control unit 71 transmits the operation history information J1 to the electronic device 3 at a time point t3 after the nebulization unit 73 is stopped.

Upon receiving the operation history information J1 from the nebulizer 1, the electronic device 3 transfers the operation history information J1 to the management server 6. In the management server 6, the operation history information J1 is recorded in the database 63.

FIG. 7 is a timing chart for explaining the operation of the nebulizer control unit 71 when a treatment is completed by two operations of the nebulization unit 73 (when the treatment is interrupted once).

Upon detecting the start operation at a time point t4, the nebulizer control unit 71 activates the nebulization unit 73. Upon detecting the end operation at a time point t5, the nebulizer control unit 71 stops the operation of the nebulization unit 73 and generates operation history information J2 relating to the operation of the nebulization unit 73 started at the time point t4. The operation history information J2 includes three types of information, that is, the time point t4 (operation starting time point), a time difference between the time point t4 and the time point t5 (operation time period of the nebulization unit 73), and a type of medicinal solution nebulized by the nebulization unit 73. The nebulizer control unit 71 transmits the operation history information J2 to the electronic device 3 at a time point t6 after the nebulization unit 73 is stopped.

Then, upon detecting the start operation at a time point t7, the nebulizer control unit 71 activates the nebulization unit 73. Upon detecting the end operation at a time point t8, the nebulizer control unit 71 stops the operation of the nebulization unit 73 and generates operation history information J3 relating to the operation of the nebulization unit 73 started at the time point t7. The operation history information J3 includes three types of information, that is, the time point t7 (operation starting time point), a time difference between the time point t7 and the time point t8 (operation time period of the nebulization unit 73), and a type of medicinal solution nebulized by the nebulization unit 73. The nebulizer control unit 71 transmits the operation history information J3 to the electronic device 3 at a time point t9 after the nebulization unit 73 is stopped.

Upon receiving the operation history information J2 and J3 from the nebulizer 1, the electronic device 3 transfers the operation history information J2 and J3 to the management server 6. In the management server 6, the operation history information J2 and J3 is recorded in the database 63.

The server control unit 62 of the management server 6 executes a process of analyzing an operation history group including a plurality of pieces of operation history information (a plurality of pieces of operation history information including the same date) for the past one day recorded in the database 63 at a regular timing such as a time point at which a date changes. For example, in a case where the operation illustrated in FIG. 6 and the operation illustrated in FIG. 7 have been performed on a certain day, a process of analyzing an operation history group including the operation history information J1, the operation history information J2, and the operation history information J3 is executed.

Specifically, the server control unit 62 selects one piece of operation history information from an operation history group as a first operation history information, and selects operation history information acquired (recorded in the database 63) subsequently to the first operation history information from the operation history group as a second operation history information. The server control unit 62 makes a determination whether the first operation history information and the second operation history information are information corresponding to a case where the nebulization unit 73 has operated for an identical treatment based on a time difference between an ending time point of an operation period (referred to as a first operation period) of the nebulization unit 73 according to the first operation history information and a starting time point of an operation period (referred to as a second operation period) of the nebulization unit 73 according to the second operation history information (an interval between successively-performed two operations of the nebulization unit 73, hereinafter referred to a time difference T). The server control unit 62 derives the ending time point of the first operation period corresponding to the first operation history information from the operation starting time point and the operation time period included in the first operation history information, and derives the above-described time difference T from the derived ending time point and the operation starting time point included in the second operation history information.

The server control unit 62 repeats the above-described process such that each piece of operation history information excluding the latest operation history information included in the operation history group is selected as the first operation history information. Whether each piece of operation history information is old or new can be determined by referring to the information of the operation starting time points included therein or by referring to the date and time when each piece of operation history information has been recorded in the database 63. In a case where the operation history group includes the operation history information J1, the operation history information J2, and the operation history information J3, the server control unit 62 makes the above-described determination by selecting the operation history information J1 as the first operation history information and the operation history information J2 as the second operation history information, and makes the above-described determination by selecting the operation history information J2 as the first operation history information and the operation history information J3 as the second operation history information.

In a case where the treatment using the nebulizer 1 has been interrupted, the time difference T (the time difference between the time point t5 and the time point t7 in the example of FIG. 7) is not so long. Thus, when the time difference T is equal to or longer than a predetermined threshold value TH, the server control unit 62 determines that the first operation history information and the second operation history information are information corresponding to a case where the nebulization unit 73 has operated for different treatments. When the time difference T is shorter than the threshold value TH, the server control unit 62 determines that the first operation history information and the second operation history information are information corresponding to a case where the nebulization unit 73 has operated for an identical treatment.

The server control unit 62 records each of a plurality of pieces of operation history information determined to be operation history information corresponding to a case where the nebulization unit 73 has operated for an identical treatment in association with common identification information. For example, in a case where the operation history group includes the operation history information J1, the operation history information J2, and the operation history information J3, the server control unit 62 records the operation history information J2 and the operation history information J3 in association with common identification information.

For a plurality of pieces of operation history information to which common identification information is added out of the operation history group recorded in the database 63, the server control unit 62 performs a combining process of combining these plurality of pieces of operation history information. In the example of FIG. 7, the server control unit 62 calculates, for example, a total value of the operation time period included in the operation history information J2 and the operation time period included in the operation history information J3, and generates operation history information J2A including the total value, the operation starting time point of the nebulization unit 73 included in the operation history information J2, and the medicinal solution type information included in the operation history information J2. Then, the server control unit 62 deletes the operation history information J2 and J3, and records the operation history information J2A in the database 63 instead.

Instead of the combining process, the server control unit 62 may perform a deleting process of retaining only one of the plurality of pieces of operation history information to which the common identification information is added and deleting the rest of the plurality of pieces of operation history information. In the example of FIG. 7, the server control unit 62 may delete the operation history information J2 or delete the operation history information J3 out of the operation history information J2 and the operation history information J3, for example.

Advantageous Effects of Treatment Management System

In the treatment management system 100, based on two pieces of operation history information adjacent to each other in a time series order acquired by the management server 6, it is determined whether the two pieces of operation history information are information related to the operations of the nebulization unit 73 for an identical treatment. When it is determined that the two pieces of operation history information are information related to the operations of the nebulization unit 73 for an identical treatment, correction of the two pieces of operation history information is performed (the combining process or the deleting process described above). With such a configuration, after the analysis process, one piece of operation history information is always recorded for every one treatment in the database 63. Accordingly, for example, a physician or the like can grasp the frequency of the treatment using the nebulizer 1 by referring to the operation history information recorded in the database 63, which is helpful for determining a treatment strategy.

In addition, in a case where the above-described combining process is performed, an inhalation amount of a medicinal solution in one treatment can be roughly grasped based on the operation time period included in the operation history information after the combining process. Accordingly, a physician can determine whether an appropriate treatment has been performed by a user, which is helpful for determining a treatment strategy.

The nebulizer 1 of the treatment management system 100 transmits operation history information at a time point (time point t3 in FIG. 6, time points t6 and t9 in FIG. 7) after the operation of the nebulization unit 73 is stopped. In this way, since the transmission of the operation history information is performed in a state where the ultrasonic vibrator 41 of the nebulization unit 73 is not in operation, the transmission can be stably performed without being affected by the operation noise of the nebulization unit 73. Accordingly, the operation history information can be transmitted to the management server 6 without omission, and the management of treatment can be appropriately performed.

First Modification of Treatment Management System

The server control unit 62 may be configured not to perform both the combining process and the deleting process. Even in this case, operation history information for each treatment can be identified by identification information added to each operation history information recorded in the database 63. That is, by viewing a plurality of pieces of operation history information to which common identification information is added, a physician can recognize that these pieces of operation history information are information generated for one treatment. Thus, even in this modification, a physician can determine whether an appropriate treatment has been performed by a user, which is helpful for determining a treatment strategy.

Second Modification of Treatment Management System

The server control unit 62 may request a user terminal (the electronic device 3 or another device connected to the network 4) to confirm whether to correct a plurality of pieces of operation history information associated with common identification information (to perform the combining process or the deleting process), and may perform the combining process or the deleting process when the correction is determined to be necessary depending on a response to the request. In this way, by performing correction after confirming with a user, it is possible to prevent, with high accuracy, the plurality of pieces of operation history information from being erroneously corrected. As a result, the frequency at which the treatment has been performed can be more accurately provided to a physician.

Third Modification of Treatment Management System

The server control unit 62 may determine whether the first operation history information and the second operation history information are information corresponding to a case where the nebulization unit 73 has operated for an identical treatment based on a time difference T, the medicinal solution type information included in the first operation history information, and the medicinal solution type information included in the second operation history information.

Even when the time difference T, which is the interval between successively-performed two operations of the nebulization unit 73, is short, if the types of medicinal solutions nebulized in the two operations are different, it can be said that the two operations have operations of the nebulization unit 73 performed for different treatments. Thus, when the time difference T is shorter than a threshold value TH and the medicinal solution type information included in the first operation history information is different from the medicinal solution type information included in the second operation history information, the server control unit 62 determines that the first operation history information and the second operation history information are information corresponding to a case where the nebulization unit 73 has operated for different treatments. On the other hand, when the time difference T is shorter than the threshold value TH and the medicinal solution type information included in the first operation history information is the same as the medicinal solution type information included in the second operation history information, the server control unit 62 determines that the first operation history information and the second operation history information are information corresponding to a case where the nebulization unit 73 has operated for an identical treatment.

In this way, whether the treatment has been interrupted can be determined with higher accuracy by considering not only the interval between the operation periods of the nebulization unit 73 which has successively operated, but also the type of medicinal solution nebulized during each of the operation periods.

Fourth Modification of Treatment Management System

In the above description, it is assumed that the server control unit 62 acquires operation history information from the nebulizer 1, records the operation history information in the database 63, and analyzes the operation history information recorded in the database 63. However, the nebulizer control unit 71 of the nebulizer 1 may have the function of the server control unit 62. The treatment management system of the present modification has a configuration in which the management server 6 is removed from the treatment management system 100. In the present modification, the nebulizer control unit 71 constitutes a management device.

In the treatment management system of the present modification, the nebulizer control unit 71 of the nebulizer 1 generates operation history information of the nebulization unit 73 every time the nebulization unit 73 operates, and records the operation history information in a built-in ROM. The nebulizer control unit 71 executes a process of analyzing an operation history group including a plurality of pieces of operation history information for the past one day recorded in the ROM at a regular timing such as a time point at which a date changes. This process is the same as the process performed by the server control unit 62 described above.

In this way, by determining whether the treatment has been interrupted in the nebulizer 1, one piece of operation history information is always recorded for every one treatment in the ROM of the nebulizer 1. Therefore, a physician or the like can grasp the frequency of the treatment using the nebulizer 1 by reading out the operation history information analyzed and recorded in the ROM, for example, via the electronic device 3, and referring to the operation history information, which is helpful for determining a treatment strategy. Also in the present modification, the nebulizer control unit 71 may be configured not to perform both the combining process and the deleting process.

Fifth Modification of Treatment Management System

In the above-described fourth modification, it is assumed that the nebulizer control unit 71 determines whether the treatment has been interrupted, and corrects the operation history information in accordance with the determination result. As a modification thereof, the nebulizer control unit 71 may determine whether the treatment has been interrupted, and may control transmission of operation history information to the management server 6 in accordance with the determination result. The treatment management system of the present modification has a configuration in which the management server 6 is added to the configuration of the treatment management system of the fourth modification. The management server 6 in the present modification records operation history information transmitted from the nebulizer 1 in the database 63, generates data based on the recorded information, and provides the data to a user terminal or the like.

After generating operation history information, the nebulizer control unit 71 sets the generated latest operation history information as the second operation history information, and sets operation history information generated immediately before the latest operation history information as the first operation history information. Then, the nebulizer control unit 71 determines whether the first operation history information and the second operation history information are information corresponding to a case where the nebulization unit 73 has operated for an identical treatment. This determination method is the same as the determination method performed by the server control unit 62 of the above-described embodiment. Only when it is determined that the first operation history information and the second operation history information are not information corresponding to a case where the nebulization unit 73 has operated for an identical treatment, the nebulizer control unit 71 transmits the second operation history information to the electronic device 3. That is, when it is determined that the first operation history information and the second operation history information are information corresponding to a case where the nebulization unit 73 has operated for an identical treatment, the nebulizer control unit 71 omits transmission of the second operation history information to the electronic device 3.

FIG. 8 is a timing chart for explaining a modification of the operation of the nebulizer control unit 71 when a treatment is completed by two operations of the nebulization unit 73. FIG. 8 is different from FIG. 7 in that the transmission of the operation history information J3 after the time point t8 is omitted. A time difference T derived from the operation history information J2 generated at the time point t5 and the operation history information J1 generated immediately therebefore as illustrated in FIG. 6 is equal to or longer than a threshold value. Thus, the operation history information J2 generated at the time point t5 is transmitted to the electronic device 3 at the subsequent time point t6. On the other hand, a time difference T derived from the operation history information J3 generated at the time point t8 and the operation history information J2 generated immediately therebefore is shorter than the threshold value. Thus, the operation history information J3 generated at the time point t8 is not transmitted to the electronic device 3.

According to the present modification, when the treatment has been interrupted, only the operation history information (the operation history information J2 in the example of FIG. 8) related to the operation of the nebulization unit 73 from the start of the treatment to the interruption of the treatment is transmitted to the electronic device 3. Thus, one piece of operation history information is always recorded for every one treatment in the database 63 of the management server 6. As a result, the frequency of the treatment using the nebulizer 1 can be accurately grasped.

In addition, according to the present modification, the frequency of transmission of data from the nebulizer 1 can be reduced, and thus, if the nebulizer is operated by a battery, the continuous use time thereof can be extended. In addition, it is not necessary to determine whether a treatment has been interrupted and correct operation history information in the management server 6. Accordingly, the processing load of the management server 6 can be reduced. Further, a required capacity of the database 63 can be reduced.

Modification of Operation History Information

In the above description, it is assumed that operation history information (J1, J2, J3) includes an operation starting time point of the nebulization unit 73 (a time point at which a start operation is detected), an operation time period of the nebulization unit 73, and a type of medicinal solution nebulized by the nebulization unit 73. However, as the operation history information, operation history information IF1 to IF3 described below may be used.

The operation history information IF1 includes an operation starting time point of the nebulization unit 73, an operation ending time point of the nebulization unit 73 (a time point at which an end operation is detected), and a medicinal solution type. When the operation history information IF1 is used, a time point of a treatment performed and a treatment time can be managed by determining an operation time period of the nebulization unit 73 based on the operation starting time point and the operation ending time point.

The operation history information IF2 includes an operation ending time point of the nebulization unit 73, an operation time period of the nebulization unit 73, and a medicinal solution type. When the operation history information IF2 is used, the above-described time difference T can be derived by determining an operation starting time point of the nebulization unit 73 based on the operation ending time point and the operation time period.

The operation history information IF3 includes an operation time period of the nebulization unit 73 and a medicinal solution type. When the operation history information IF3 is used, the above-described time difference T can be derived by considering a time point at which the operation history information IF3 is received in the management server 6 or a time point at which the operation history information IF3 is recorded in the nebulizer 1 as an operation ending time point of the nebulization unit 73.

A medicinal solution type need not be included in the operation history information (J1, J2, J3) described in the embodiment and each of the operation history information IF1 to IF3 of the modification. Even in this case, if it is assumed that a treatment is performed using a single type of medicinal solution, a time point of the treatment performed and a treatment time can be managed.

Further, in the treatment management system, there may be a case where only a treatment frequency and a medicinal solution type are managed and the management of a treatment time is not required. In that case, operation history information IF4 including an operation starting time point of the nebulization unit 73 and a medicinal solution type may be used. When the operation history information IF4 is used, the above-described time difference T can be derived by considering a time point at which the operation history information IF4 is received in the management server 6 or a time point at which the operation history information IF4 is recorded in the nebulizer 1 as an operation ending time point of the nebulization unit 73. Also in the operation history information IF4, when the management of a medicinal solution type is unnecessary, the medicinal solution type can be omitted.

Modification of Transmission Time Point of Operation History Information

In the above description, in a configuration in which the nebulizer 1 has a function of transmitting operation history information to the electronic device 3, the transmission time point of the operation history information is set to a time point after the operation of the nebulization unit 73 is stopped. As a modification, the nebulizer control unit 71 may transmit part of operation history information to the electronic device 3 at a time point at which the start operation is detected, and transmit the rest of the operation history information to the electronic device 3 at a time point after the operation of the nebulization unit 73 is stopped in response to the end operation.

For example, when transmitting the operation history information J1, the nebulizer control unit 71 may transmit the information of an operation starting time point to the electronic device 3 at a time point at which the start operation is detected, and transmit the information of an operation time period and a medicinal solution type to the electronic device 3 at a time point after the nebulization unit 73 is stopped in response to the end operation. Even in that case, for example, when the transmission of the operation starting time point is not successful, the time difference T can be derived by considering a time point at which the management server 6 receives the information of the operation time period and the medicinal solution type out of the operation history information J1 as an operation ending time point. According to this configuration, the operation history information can be efficiently transmitted to an external device.

In the treatment management system 100 of the embodiment and the modifications thereof, the electronic device 3 may be omitted, and the nebulizer 1 and the management server 6 may communicate with each other via the network 4. Alternatively, the management server 6 may be omitted, and the function of the management server 6 may be implemented by a treatment management application installed in the electronic device 3. That is, the electronic device 3 may be configured to record and analyze operation history information.

While various embodiments have been described with reference to the drawings, needless to say, the present invention is not limited to such examples. It will be apparent to those skilled in the art that various changes and modifications can be made within the scope of the claims, and it is understood that these are naturally belong within the technical scope of the present invention. Further, components of the above-described embodiments may be combined as desired within a range that does not depart from the spirit of the present invention.

Note that the present application is based on Japanese Patent Application filed on Dec. 23, 2020 (JP 2020-213867), the content of which is incorporated herein by reference.

REFERENCE NUMERALS LIST

100 Treatment management system
1 Nebulizer
50 Operating member
51 Start/End button
71 Nebulizer control unit
73 Nebulization unit
3 Electronic device
4 Network
6 Management server
62 Server control unit

What is claimed is:

1. A system, comprising:
a therapeutic inhaler configured to enable inhalation of a medicinal solution nebulized by a nebulization unit, the therapeutic inhaler comprising:

the nebulization unit including a vibrating portion and a mesh portion configured to nebulize and spray the medicinal solution;
a therapeutic inhaler communication unit including a therapeutic inhaler communication interface;
an operating member configured to enable a start operation for instructing a start of nebulization by the nebulization unit and an end operation for instructing an end of the nebulization by the nebulization unit; and
an inhaler processor configured to transmit operation history information of the nebulization unit to a management device,
the inhaler processor transmitting at least part of the operation history information to the management device at a time point after the nebulization unit is stopped in response to the end operation; and
the management device comprising:
a management device communication unit including a management device communication interface configured to communicate with the therapeutic inhaler; and
a processor,
the processor being configured to
acquire operation history information of the nebulization unit including the vibrating portion and the mesh portion in the therapeutic inhaler enabling inhalation of the medicinal solution nebulized by the nebulization unit, the operation history information including first operation history information and second operation history information acquired subsequently to the first operation history information the operation history being transmitted from the therapeutic inhaler communication unit of the therapeutic inhaler to the management device communication unit,
determine whether the first operation history information and the second operation history information are information corresponding to a case where the nebulization unit has operated for an identical treatment, the identical treatment being a treatment when the processor has determined that a time difference between two operations of the nebulization unit is equal to or shorter than a threshold value, the identical treatment based on a time difference between an ending time point of a first operation period of the nebulization unit according to the first operation history information and a starting time point of a second operation period of the nebulization unit according to the second operation history information,
record the first operation history information and the second operation history information in association with common identification information upon determining that the first operation history information and the second operation history information are information corresponding to a case where the nebulization unit has operated for an identical treatment, and
determine a treatment strategy based upon determining that the first operation history information and the second operation history information are information corresponding to the case where the nebulization unit has operated for an identical treatment,
wherein the therapeutic inhaler communication unit including the therapeutic inhaler communication interface is configured to be communicable with the management device communication unit.

2. The management device according to claim 1, wherein the processor determines that the first operation history information and the second operation history information are information corresponding to a case where the nebulization unit has operated for different treatments when the time difference is equal to or longer than a threshold value, and determines that the first operation history information and the second operation history information are information corresponding to a case where the nebulization unit has operated for an identical treatment when the time difference is shorter than the threshold value.

3. The management device according to claim 1, wherein
the operation history information includes medicinal solution type information indicating a type of medicinal solution nebulized by the nebulization unit during an operation period of the nebulization unit, and
the processor determines whether the first operation history information and the second operation history information are information corresponding to a case where the nebulization unit has operated for an identical treatment based on the time difference, the medicinal solution type information included in the first operation history information, and the medicinal solution type information included in the second operation history information.

4. The management device according to claim 3, wherein the processor determines that the first operation history information and the second operation history information are information corresponding to a case where the nebulization unit has operated for different treatments when the time difference is longer than a threshold value and the medicinal solution type information included in the first operation history information differs from the medicinal solution type information included in the second operation history information.

5. The management device according to claim 1, wherein the processor
transmits a request to a user terminal to confirm whether correction of a plurality of pieces of the operation history information associated with the common identification information is necessary,
receives a response to the request that was transmitted, and,
upon determining that the correction is necessary based on the response to the request, corrects the plurality of pieces of the operation history information.

6. The management device according to claim 5, wherein the processor
performs the correction by deleting the plurality of pieces of the operation history information except for one of the plurality of pieces of the operation history information, or
performs the correction by combining the plurality of pieces of the operation history information.

7. A system comprising:
a management device including a processor; and
a nebulization unit including a vibrating portion and a mesh portion,
the processor being configured to, for each start and end operation of the nebulization unit,
store an operation starting time point as a time the nebulization unit is activated,
store an operation stopping time point as a time the nebulization unit is stopped,
calculate an operation time period of the nebulization unit as a difference between the operation starting time point and the operation stopping time point, store the operation time period,
the processor further configured to:
acquire operation history information of the nebulization unit in a therapeutic inhaler configured to enable inhalation of a medicinal solution nebulized by the nebulization unit, the operation history information including first operation history information, including the operation time period that was calculated for the start and end operation of the nebulization unit, and second operation history information, including an operation time period that was calculated for a subsequent start and end operation of the nebulization unit, acquired subsequently to the first operation history information,
determine whether the first operation history information and the second operation history information are information corresponding to a case where the nebulization unit has operated for an identical treatment, the identical treatment being a treatment when the processor has determined that the time difference between two operations of the nebulization unit is equal to or shorter than a threshold value, the identical treatment based on a time difference between an ending time point of a first operation period of the nebulization unit according to the first operation history information and a starting time point of a second operation period of the nebulization unit according to the second operation history information,
control transmission of the operation history information to an external device, and
upon determining that the first operation history information and the second operation history information are information corresponding to a case where the nebulization unit has operated for an identical treatment at a time point before transmission of the second operation history information to the external device, omit the transmission of the second operation history information to the external device.

8. The system according to claim 7, wherein the processor determines that the first operation history information and the second operation history information are information corresponding to a case where the nebulization unit has operated for different treatments when the time difference is equal to or longer than a threshold value, and determines that the first operation history information and the second operation history information are information corresponding to a case where the nebulization unit has operated for an identical treatment when the time difference is shorter than the threshold value.

9. The system according to claim 7, wherein the operation history information includes medicinal solution type information indicating a type of medicinal solution nebulized by the nebulization unit during an operation period of the nebulization unit, and the processor determines whether the first operation history information and the second operation history information are information corresponding to a case where the nebulization unit has operated for an identical treatment based on the time difference, the medicinal solution type information included in the first operation history information, and the medicinal solution type information included in the second operation history information.

10. The system according to claim 9, wherein the processor determines that the first operation history information and the second operation history information are information corresponding to a case where the nebulization unit has operated for different treatments when the time difference is longer than a threshold value and the medicinal solution type information included in the first operation history information differs from the medicinal solution type information included in the second operation history information.

11. A non-transitory computer readable storage medium storing a management program for managing a treatment using a therapeutic inhaler configured to enable inhalation of a medicinal solution nebulized by a nebulization unit, the therapeutic inhaler comprising a nebulization unit including a vibrating portion and a mesh portion, the management program causing a computer processor to execute processing, the processing comprising:

for each start and end operation of the nebulization unit,
    storing an operation starting time point as a time the nebulization unit is activated,
    storing an operation stopping time point as a time the nebulization unit is stopped,
    calculating an operation time period of the nebulization unit as a difference between the operation starting time point and the operation stopping time point,
    storing the operation time period,
the processing further including:
acquiring operation history information of the nebulization unit via a communication unit of the therapeutic inhaler, the operation history information including first operation history information, including the operation time period that was calculated for the start and end operation of the nebulization unit, and second operation history information, including an operation time period that was calculated for a subsequent start and end operation of the nebulization unit, acquired subsequently to the first operation history information;
determining whether the first operation history information and the second operation history information are information corresponding to a case where the nebulization unit has operated for an identical treatment, the identical treatment being a treatment when the processor has determined that the time difference between two operations of the nebulization unit is equal to or shorter than a threshold value, the identical treatment based on a time difference between an ending time point of a first operation period of the nebulization unit according to the first operation history information and a starting time point of a second operation period of the nebulization unit according to the second operation history information; and
recording the first operation history information and the second operation history information in association with common identification information upon determining that the first operation history information and the second operation history information are information corresponding to a case where the nebulization unit has operated for an identical treatment.

12. A non-transitory computer readable storage medium storing a management program for managing a treatment using a therapeutic inhaler configured to enable inhalation of a medicinal solution nebulized by a nebulization unit including a vibrating portion and a mesh portion, the management program causing a computer processor to execute processing, the processing comprising:

for each start and end operation of the nebulization unit,
    store an operation starting time point as a time the nebulization unit is activated,
    store an operation stopping time point as a time the nebulization unit is stopped,
    calculate an operation time period of the nebulization unit as a difference between the operation starting time point and the operation stopping time point,
    store the operation time period,
acquiring operation history information of the nebulization unit, the operation history information including first operation history information, including the operation time period that was calculated for the start and end operation of the nebulization unit, and second operation history information, including an operation time period that was calculated for a subsequent start and end operation of the nebulization unit, acquired subsequently to the first operation history information;
determining whether the first operation history information and the second operation history information are information corresponding to a case where the nebulization unit has operated for an identical treatment, the identical treatment being a treatment when the processor has determined that the time difference between two operations of the nebulization unit is equal to or shorter than a threshold value, the identical treatment based on a time difference between an ending time point of a first operation period of the nebulization unit according to the first operation history information and a starting time point of a second operation period of the nebulization unit according to the second operation history information; and
upon determining that the first operation history information and the second operation history information are information corresponding to a case where the nebulization unit has operated for an identical treatment at a time point before transmission of the second operation history information to an external device, omitting the transmission of the second operation history information to the external device.

* * * * *